United States Patent [19]

Fattori et al.

[11] 4,016,211
[45] Apr. 5, 1977

[54] STABILIZED POLYGLYCOL FOR HIGH TEMPERATURES

[75] Inventors: Silvano Fattori; Enzo Rossi, both of San Donato Milanese; Luigi Imparato, Milan, all of Italy

[73] Assignee: Snam Progetti S.p.A., Milan, Italy

[22] Filed: July 3, 1975

[21] Appl. No.: 592,728

[30] Foreign Application Priority Data

July 4, 1974  Italy .................................. 24790/74

[52] U.S. Cl. .......................... 260/611.5; 260/620; 260/613 R; 260/592
[51] Int. Cl.² ........................................ C07C 43/00
[58] Field of Search .............................. 260/611.5

[56] References Cited

UNITED STATES PATENTS

| 2,641,614 | 6/1953 | Britton et al. ............ 260/611.5 UX |
| 2,687,378 | 8/1954 | Goldschmidt et al. ..... 260/611.5 X |
| 2,736,709 | 2/1956 | Glickman et al. ........ 260/611.5 UX |
| 2,942,033 | 6/1960 | Leis et al. ..................... 260/611.5 |

*Primary Examiner*—Bernard Helfin
*Attorney, Agent, or Firm*—Ralph M. Watson

[57] ABSTRACT

A composition comprising a poly-alkyleneglycol is stablized against molecular degradation and viscosity loss at elevated temperatures by about 0.1 to about 10% by weight of an arylhydroquinone such as p-acetylphenylhydroquinone.

12 Claims, No Drawings

STABILIZED POLYGLYCOL FOR HIGH TEMPERATURES

This invention relates to the stabilization of polyglycols against oxidation at high temperatures.

More particularly this invention relates to polyalkylene clycol compositions, wherein the degradation of the molecules and viscosity loss are substantially inhibited.

It is known that generally the polyglycols are compounds which possess properties which make it advantageous to use them in many applications. They have good lubricating properties, high viscosity index, low pour point, good diathermic properties, negligible corrosion effect on the metals.

For this reason they are usually employed also as hydraulic fluids, as lubricants for engines, as diathermic fluids.

Unfortunately they have poor stability against oxidation and even at low temperatures, at about 35° C, they oxidize in air.

Their poor stability against oxidation is due to an easy formation of hydroperoxides because of the presence in the molecules of C-H links, adjacent to oxygen atoms, which are particularly reactive towards the radicals propagators of oxidation chains.

The formed hydroperoxides are thermally unstable and their decomposition causes the rupture of the macromolecule and, the formation of volatile fragments with a consequent loss of viscosity and weight of the polyglycol. A moderate temperatures stabilization against oxidation does not present any problem since also the most usual anti-oxidants such as 2,6-di-ter-butyl-p-cresole, hydroquinone, phenylalpha-naphthylamine, sufficiently efficacious.

However inhibition becomes a problem at temperatures higher than 150° C when these inhibitors of free radicals lose their effectiveness. According to the opinion of some piople this is due to the fact that the same inhibitors at these temperatures are made inactive by direct oxidation through oxygen.

But the main reason they are ineffective is a direct consequence of the instability of the hydroperoxides formed in the first phase of the oxidation, which upon decomposing set free a large number of radicals, which rapidly exhaust the inhibitors.

It has been now found, which is the subject of this invention, that the polyglycols may be effectively stabilized against molecular degradation and also the loss of viscosity at high temperatures (> 150° C) through compounds of the aryl-hydroquinone class having the following general formula:

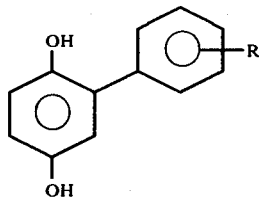

wherein R may be selected from hydrogen, alkyl, aryl, condensed aryl, arylalkyl, hydroxyl, substituted hydroxyl, amine, substituted amine, carboxyl, substituted carboxyl, aldehyde, carbonyl alkyl, carbonyl aryl, cyano, nitro group and halogen.

The amounts of stabilizer employed may depend on the structure of the polyglycol and on the type of the application wherein it is used 0.001% by weight to about 10%, preferably from about 0.1% to about 2%.

The preparation of the derivatives of the arylhydroquinones of the present invention is widely described in the literature. For instance it may be carried out according to the method described by D. E. Kvalnes, J. Am. Chem. Soc., 56, 2478 (1934).

For the purpose of better showing this invention some specific examples are reported which however are not limitative thereof.

EXAMPLE 1

18.3 ml aniline were diazotized in the conventional way in a minimum quanity of water.

The solution of the resulting diazonium salt was slowly added to a suspension vigorously stirred of 18grams p-benzoquinone in 500 ml water, containing an excess of sodium dicarbonate and kept at a temperature of 15° C.

An evolution of nitrogen was noticed and phenylquinone was separated from the mixture. The yield of the raw product isolated through filtration and washed with 1 l water was 79%. After crystallization from ligroine a melting point of 112 to 113° C was found.

Afterwards the phenylquinone was reduced to phenylhydroquinone by using an excess of sodium hydrosulfite in a hydroalcohol solution. After extraction whith chloroform the phenyl hydroquinone was crystallized from methylene chloride; melting point: 96 - 98° C.

EXAMPLE 2

17 grams o-phenylphenol, dissolved in a 10% NaOH solution were oxidized at the temperature of 15 - 20° C by means of an addition under stirring, of a saturated aqueous solution containing 26 g of potassium persulfate.

The resulting mixture was left to settle overnight and subsequently was neutralized and filtered.

Said solution was then treated with an excess of HC1, heated while boiling up for two hours, cooled and extracted with ether. The ether evaporation left a residue, consisting of the raw phenylhydroquinone with a 32% yield.

After the crystallization of the product from methylene chloride a melting point of 94 - 96° C was found.

EXAMPLE 3

By operating under the same conditions described in example 1 starting from -p-methylaniline and o-benzoquinone the p-methylphenylquinone was prepared, having a yield of 65%, melting point 136–137° C (crystallyzation solvent: ligroine) and by reducing the resulting product the p-methylphenylhydroquinone was obtained having a melting point of 116° – 117° C (crystallization solvent = methylene chloride).

EXAMPLE 4

By operating under the conditions described in example 1, starting from p-methoxyaniline and p-benzoquinone the p-methoxyphenylquinone was prepared, the yield being 91%, melting point 119° – 120° C (crystallization solvent being water/alcohol) and by reducing this the p-methoxy phenylhydroquinone was obtained with a melting point of 108°–109° C (crystallization solvent being the methylene chloride).

EXAMPLE 5

By operating under the same conditions described in example 1, starting from p-acetyl-aniline and p-benzoquinone, the p-acetylphenylquinone was prepared, yield: 88%, melting point: 151° – 152° C (crystallization solvent: ligroin/chloroform) and through the reduction thereof the p-acetylphenylhydroquinone was obtained having a melting point of 190° – 191° C (crystallization solvent methylenechloride).

EXAMPLE 6

The extraordinary efficaciousness of the arylhydroquinones in protection of the polyglycols against the oxidation was shown then by comparing their induction periods with the ones relative to the frequently used anti-oxidants, in the tests of oxygen absorption.

The tests were carried out with an apparatus analogous to the one described by M. A. M. Bradney, A. D. Forbes (Chem. Ind. 15, 495, 1970): a constant air-flow was caused to pass on the sample under examination, kept under vigorous stirring by a magnetic small bar rotating in a double wall cell, which was thermostatically maintained at the test temperature by means of an oil circulation.

The absorption of oxygen was revealed by an $O_2$ percentage analyser, the electric signal of which was elaborated by an electronic complex which automatically records the absorption velocity and the total absorption of oxygen.

The induction period measured by means of this apparatus was fixed as the time at which is observed the beginning of a sudden increase of the oxidation rate depending on the end of the inhibiting power.

The results of the tests carried out at 197° ± 0.2° C, on samples of 3 grams based on polypropyleneglycol having a molecular weight of 1400, stirred at 1000 r.p.m. by using an air flow of 50 cm³/min are shown in table 1.

TABLE 1

Oxidation tests in air flow (50 cm³/min) at 197° C
Base oil: polypropyleneglycol (molecular weight = 1400)

| Additive | Induction time (min) 0.5% | 1% | 2% (P/P) |
|---|---|---|---|
| 2,6 di-tert butyl-4-methylphenol | 1 | 2 | 22 |
| phenyl alpha naphthylamine | 1 | 3 | 120 |
| 3,6-dioctylphenothiazine | 10 | 70 | 210 |
| hydroquinone | 45 | 90 | 140 |
| tert-butylhydroquinone | 32 | 53 | 87 |
| pyrocatechol | 1 | 3 | 40 |
| phenylhydroquinone | 60 | 175 | 410 |
| p-methylphenylhydroquinone | 110 | 235 | 465 |
| p-methoxyphenylhydroquinone | 58 | 165 | 395 |
| p-acetylphenylhydroquinone | 75 | 315 | >500 |

EXAMPLE 7

To evidence the efficaciousness of some arylhydroquinones, of this invention, in protecting the polyglycols from degradation the determinations of viscosity and weight variations thereof after oxidation tests in the presence of copper strips are reported.

The tests consisted in causing an air flow having a uniform speed to bubble through the sample under examination. Said sample was contained in a glass cylinder wherein a copper strip was immersed, and which was thermostatically maintained at the test temperature in a heated aluminum block.

When the test was over the percentage variations of polyglycol viscosity and weight and the percentage variation of the weights of the strips were measured.

The results relative to oxidation tests carried out at temperatures of 160° ± 0.2° C on samples based on polyethylenepropyleneglycol having a molecular weight = 1500, by using an air flow of 50 cm³/min for a 96 hours period of time, are reported in table 2.

TABLE 2

Oxidation tests with air bubbling (50 cm³/min) in the presence of copper strips at a temperature = 160° C. Base oil: polyethylen-propyleneglycol (molecular weight = 1500)

| Additive | % (P/P) | Percentage variation viscosity at 37.8° C | Variation weight percentage of polyglycol | Variation weight percentage of strip |
|---|---|---|---|---|
|  | — | − 49,50 | − 77,43 | − 0,14 |
| 3,6-dioctylphenothiazine | 2 | − 21,22 | − 3,57 | − 0,03 |
| p,p'-dioctyldiphenylamine | 2 | − 41,87 | − 4,42 | − 0,03 |
| hydroquinone | 2 | − 6,99 | − 1,14 | − 0,09 |
| phenyl alpha naftylamine | 2 | − 9,80 | − 1,71 | − 0,25 |
| phenylhydroquinone | 2 | + 3,53 | − 0,25 | − 0,04 |
| p-acetylphenylhydroquinone | 2 | + 3,11 | − 0,19 | − 0,06 |
| p-methoxyphenylhydroquinone | 2 | + 2,14 | − 0,14 | − 0,07 |
| p-methylphenylhydroquione | 2 | + 2,82 | − 0,11 | − 0,09 |
| m-nitrophenylhydroquinone | 1 | − 3,80 | − 1,01 | − 0,03 |
| m-chlorophenylhydroquinone | 1 | − 2,74 | − 1,25 | − 0,02 |
| p-diphenylhydroquinone | 1 | − 5,37 | − 1,41 | − 0,11 |
| p-carboxyphenylhydroquinone | 1 | − 2,34 | − 0,87 | − 0,12 |
| β-naphthylhydroquinone | 1 | − 4,53 | − 1,07 | − 0,04 |
| p-hydroxyphenylhydroquinone | 2 | + 3,14 | − 0,17 | − 0,07 |
| p-aminophenylhydroquinone | 2 | + 3,24 | − 0,18 | − 0.08 |

What we claim is:

1. A composition comprising a polyalkyleneglycol stabilized against molecular degradation and viscosity loss at elevated temperatures by about 0.1 to about 10% by weight of an arylhydroquinone having the following general formula:

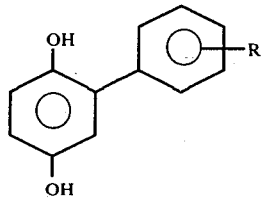

wherein R is a member of the group consisting of hydrogen, alkyl, aryl, hydroxyl, substituted hydroxyl, amine, carboxyl, substituted carboxyl, nitro and halogen.

2. A composition and as claimed in claim 1, wherein said arylhydroquinone is p-acetylphenylhydroquinone.

3. A composition and as claimed in claim 1, wherein said arylhydroquinone is p-methylphenylhydroquinone.

4. A composition as claimed in claim 1, wherein the arylhydroquinone is p-methoxyphenylhdroquinone.

5. A composition as claimed in claim 1, wherein said arylhydroquinone is phenylhydroquinone.

6. A composition as claimed in claim 1, wherein said arylhydroquinone is m-nitrophenylhydroquinone.

7. A composition as claimed in claim 1, wherein said arylhydroquinone is m-chlorophenylhydroquinone.

8. A composition as claimed in claim 1, wherein said arylhydroquinone is p-diphenylhydroquinone.

9. A composition as claimed in claim 1, wherein said arylhydroquinone is p-carboxyphenylhydroquinone.

10. A composition as claimed in claim 1, wherein said arylhydroquinone is $\beta$-naphthylhydroquinone.

11. A composition as claimed in claim 1, wherein said arylhydroquinone is p-hydroxyphenylhydroquinone.

12. A composition as claimed in claim 1, wherein said arylhydroquinone is p-aminophenylhydroquinone.

* * * * *

UNITED STATES PATENT AND TRADEMARK OFFICE
CERTIFICATE OF CORRECTION

PATENT NO. : 4,016,211
DATED : April 5, 1977
INVENTOR(S) : Silvano Fattori, Enzo Rossi and Luigi Imparato It is certified that error appears in the above-identified patent and that said Letters Patent are hereby corrected as shown below:

Column 1, line 35, Before "sufficiently" insert --are--.

line 39, Correct spelling of "people".

Column 2, line 52, Correct "-p-methylaniline" to read

--p-methylaniline--.

Column 3, line 16, Before "frequently" insert --most--.

Table 2, fourth column, first entry, Correct "-77,43" to read -- -7,43--.

Column 5, lines 16 and 18, After "composition" delete "and".

Column 6, line 2, Correct spelling of "p-methoxyphenylhydroquinone".

Signed and Sealed this

Twenty-second Day of November 1977

[SEAL]

Attest:

RUTH C. MASON
Attesting Officer

LUTRELLE F. PARKER
Acting Commissioner of Patents and Trademarks